United States Patent [19]

Hopp et al.

[11] Patent Number: 4,851,341
[45] Date of Patent: Jul. 25, 1989

[54] IMMUNOAFFINITY PURIFICATION SYSTEM

[75] Inventors: Thomas P. Hopp; Kathryn S. Prickett, both of Seattle, Wash.

[73] Assignee: Immunex Corporation, Seattle, Wash.

[21] Appl. No.: 944,261

[22] Filed: Dec. 19, 1986

[51] Int. Cl.[4] .................. C12P 21/00; C12N 15/00; C12N 5/00; C07K 13/00
[52] U.S. Cl. .................................. 435/68; 435/172.3; 435/240.27; 435/320; 530/387; 935/95; 935/104; 935/108
[58] Field of Search ................... 435/68, 172.3, 240.27; 935/95, 104, 108; 530/387

[56] References Cited

U.S. PATENT DOCUMENTS

| | | | |
|---|---|---|---|
| 4,532,207 | 7/1985 | Brewer et al. | 435/68 |
| 4,571,421 | 2/1986 | Itakura | 536/27 |
| 4,681,848 | 7/1987 | Tsukamoto et al. | 435/240 |
| 4,703,004 | 10/1987 | Hopp et al. | 435/68 |

OTHER PUBLICATIONS

Rutter, 035384 filed 9/9/81.
Hopp et al., 150126 filed 7/31/85.
Itamura et al., *Gene*, 38: 57–64, 1985.
Livingston et al., "Immunoaffinity Chromatography of Proteins," *Methods in Enzymol.*, 70:723, (1980).
Shuman et al., "Labeling of Proteins with B-Galactosidase by Gene Fusion," *J. Biol. Chem.*, 255:168, (1980).
Reed, "Preparation of Product-Specific Antisera by Gene Fusion: Antibodies Specific for the Product of the Yest Cell-Division-Cycle Gene CDC28," *Gene*, 20:255, (1982).
Smith et al., "Chemical Synthesis and Cloning of a Poly(arginine)-Coding Gene Fragment Designed to Aid Polypeptide Purification," *Gene* 32:321, (1984).
Sassanfeld et al., "A Polypeptide Fusion Designed for the Purification of Recombinant Proteins," *Bio/Technology*, Jan. 1984, p. 76.
Maurer et al., "Antigenicity of Polypeptides (PolyAmino Acids): Calcium-Dependent and Independent Antibodies," *J. Immunol.*, 105:567, (1970).
Maurer et al., "Proteins and Polypeptides as Antigens," *Methods in Enzymol.*, 70:49, (1980).
Frankel et al., "Hydrogen Exchange Studies of a Ca$^{++}$ Dependent Sheep HSA-Anti HSA System," *Fed. Proceed.*, 36:1286, (1977).

*Primary Examiner*—Elizabeth C. Weimar
*Assistant Examiner*—Thomas D. Mays
*Attorney, Agent, or Firm*—Scott G. Hallquist; Christopher L. Wight

[57] ABSTRACT

A process is disclosed for purifying a recombinant fusion protein having an N-terminal identification sequence comprising multiple anionic amino acid residues, comprising forming a complex of the protein with a divalent cation dependent monoclonal antibody specific for the sequence, isolating the complex, and dissociating antibody and protein by selectively depleting the concentration of divalent cations in contact with the complex. A particular calcium-dependent monoclonal antibody, 4E11, is useful in an embodiment of the process which employs the identification peptide DYKDDDDK.

16 Claims, No Drawings

IMMUNOAFFINITY PURIFICATION SYSTEM

BACKGROUND OF THE INVENTION

The present invention relates to immunoaffinity chromatography systems, and particularly to immunoaffinity processes employing a monoclonal antibody having divalent cation-dependent affinity for a selected peptide determinant.

The prior art describes recombinant fusion proteins which comprise synthetic leader peptides or protein fragments linked to independently derived polypeptides. In such fusions, the leader peptide or protein fragment can facilitate protein expression and purification by providing, for example, enzymatic activity enabling identification of recombinants, an amino acid sequence recognized by cellular secretory mechanisms, or a sequence having distinctive chemical or antigenic characteristics useful in purifying the fusion protein by ion exchange, reverse phase, or affinity chromatographic media.

Itakura, U.S. Pat. No. 4,571,421, describes hybrid polypeptides consisting of a somatostatin sequence and a fragment of β-galactosidase enzyme, separated by a CnBr-cleavable site permitting separation of the two protein segments. In this system, the presence of the β-galactosidase fragment permits identification of recombinants bearing the somatostatin sequence. Schuman et al., *J. Biol. Chem.* 255:168 (1980), and Reed et al., *Gene* 20:255 (1982) disclose variations of this approach involving fusion of nucleotide sequences encoding biologically active fragments of β-galactosidase and newly isolated genes. The translated hybrid protein was isolated by reference to the physical and enzymatic properties of β-galactosidase, and used to prepare specific antisera to the product of the newly isolated genes.

Rutter, Published European Patent Application No. 35384 (1981), discloses DNA constructions used to facilitate expression of cloned DNA sequences. Among the constructions disclosed are sequences encoding fusion proteins comprising an N-terminal sequence having distinctive physical properties useful for purification, joined to a desired C-terminal portion via a sequence which can be specifically cleaved to remove the N-terminal sequence. An example of such a cleavage sequence is the peptide sequence DDDDK recognized by enterokinase. Sequences having particular properties useful for purification include polyanionic segments and polycationic segments that will bind readily to ion exchangers, and hydrophobic segments capable of binding to reverse-phase media. This reference also discloses hybrid fusion proteins comprising fragments capable of being bound by specific antibody in an affinity chromatography step.

Brewer et al., U.S. Pat. No. 4,532,207, disclose recombinant fusion proteins comprising a charged polymer of amino acids, for example, polyarginine, linked to a polypeptide of interest. Following expression in a microbial host, the fusion protein is purified by chromatography involving binding of the charged polymer to ion-exchange media. Following purification, the charged polymer is removed by controlled digestion with an exopeptidase. Smith et al., *Gene* 32:321 (1984) and Sassenfeld, *Bio/Technology,* January 1984, p. 76, also describe aspects of this approach to recombinant protein purification.

Improvements in recombinant protein expression and purification technologies are of considerable interest to the biotechnology, pharmaceutical, and chemical industries.

SUMMARY OF THE INVENTION

The present invention provides a process for purifying a recombinant fusion protein having a terminal identification sequence comprising multiple anionic amino acid residues, comprising forming a complex of the protein with a divalent cation dependent monoclonal antibody specific for the sequence, isolating the complex, and dissociating antibody and protein by selectively depleting the concentration of divalent cations in contact with the complex.

DETAILED DESCRIPTION OF THE INVENTION

The present invention provides an efficient process for protein isolation, utilizing an identification peptide having multiple anionic amino acid residues in conjunction with a cation-dependent monoclonal antibody. Such a peptide provides a highly immunogenic peptide determinant, and the presence of multiple anionic amino acid residues facilitates isolation of cation-dependent antibodies. Although both natural and synthetic anionic amino acids could conceivably be incorporated into identification peptides, aspartic acid and glutamic acid are preferred. Being natural amino acids, they can be expressed as components of recombinant polypeptides in conventional protein translation systems. Generally, terminal identification peptides comprising from 3 to 6 aspartic acid or glutamic acid residues, or mixtures thereof, are useful.

A particularly preferred embodiment of this concept involves use of the amino acid sequence Asp-Tyr-Lys-Asp-Asp-Asp-Asp-Lys, or DYKDDDDK, as an N-terminal identification peptide. This sequence is immunogenic and comprises an enterokinase recognition site. Fusion proteins expressed with an N-terminal DYKDDDDK "flag" can be purified using immobilized monoclonal antibody which specifically recognizes the flag determinant. If desired, the flag sequence can be cleaved from the remainder of the fusion protein using enterokinase; this cleavage step can be undertaken before or after separation of the bound flag ligand from the immobilized antibody.

Conventional recombinant DNA techniques are employed to construct DNA vectors encoding fusion proteins having N-terminal or C-terminal identification peptides, for example, the N-terminal DYKDDDDK flag, coupled to a polypeptide sequence to be isolated. Following expression in cultures of transformed organisms, the fusion proteins can be separated from crude extracts or culture supernatants in a single affinity step mediated by specific anti-flag antibody. The DYKDDDDK flag provides superior identification and purification performance due to the presence of both hydrophilic and aromatic residues. This combination renders flag constructions highly immunogenic and ensures that the flag determinant, even when conjugated to much larger protein molecules, remains accessible to antibody in aqueous media under physiological conditions. Additional information regarding the DYKDDDDK flag system is provided in U.S. Pat. No. 4,703,004 (application Ser. No. 573,825, filed Jan. 24, 1984), which is incorporated herein by reference.

The improvement which characterizes this invention is an antibody-antigen system in which binding is dependent upon the presence of divalent metal cations. In a particularly preferred embodiment, the calcium-dependent anti-flag monoclonal antibody produced by the hybridoma cell line designated 4E11, which is specific for DYKDDDDK flag peptide, is employed. This cell line has been deposited with the American Type Culture Collection (ATCC), Rockville, Md., USA, under accession number HB-9259. Although calcium-dependent antibodies have previously been reported, [see. e.g., Maurer et al., *J. Immun.* 105:567 (1970), and Maurer et al., *Methods Enzymol.* 70:49 (1980)] their use as immunoaffinity reagents has not been disclosed.

Cation-dependent affinity media bind ligand securely only in the presence of appropriate cation, and can be induced to release ligand by selectively depleting the concentration of divalent metal cations in contact with the complex of immobilized antibody and ligand. This can be achieved by simply washing the affinity media with a solution lacking the particular cation, or preferably, by eluting with a chelating agent such as an EDTA salt (ethylene diamine tetraacetic acid), or EGTA (ethylene glycol-bis($\beta$-aminoethyl ether) N,N,N',N'-tetraacetic acid). This approach avoids use of affinity elution methods employing high salt, low pH, or chaotropic agents, which may be irreversibly denaturing. Since elution by cation removal or depletion is highly specific for the flag-antibody complex, the recovered protein is less likely to be contaminated by extraneous proteins bound to the affinity column at sites other than the antibody combining site.

The media employed to immobilize the cation-dependent antibody can be agarose, Sepharose, acrylamide, cellulosic materials, or other suitable matrices known to those of skill in the art. Preferably, antibody is covalently bonded to media, for example, by coupling to Sepharose (Pharmacia, Uppsala, Sweden) or to Affi-Gel-10 (Bio Rad Laboratories, Richmond, Calif, USA) using a procedure involving reaction of free amino groups with N-hydroxysuccinimide esters. Kits for this purpose are commercially available; a convenient method is disclosed by Wilchek et al., *Biochemistry* 10:2828 (1971). Immunoaffinity purification procedures employed in connection with the system disclosed herein can be by batch or column chromatographic methods. In addition, numerous immunoassays for expressed fusion proteins can be devised, relying upon the specificity of the divalent cation-dependent antibody for the flag determinant.

Depending upon the particular characteristics of the monoclonal antibody which is isolated, various divalent cations may be suitable in effecting binding of antibody to antigen. Such cations could include $Ca^{++}$, $Mg^{++}$, $Mn^{++}$, $Cu^{++}$, $Ni^{++}$, $Zn^{++}$, $Cd^{++}$, $Ba^{++}$ or $Sr^{++}$. Of the foregoing, $Ca^{++}$ is more commonly found to mediate cation-dependent binding sensitivity and is therefore preferred. Generally, cation concentrations should be at least 0.3 to 1 mM to ensure effective binding. Use of an EDTA solution of at least 0.5 mM as eluant, or alternatively, a concentration greater than the effective concentration of cation, effectively reduces cation concentration to a level enabling protein release.

Synthesis of Peptide Immunogen

Synthetic identification peptides can be conjugated to fatty acid-derivatized amino acids to prepare peptide immunogens, which are presented to mice to raise anti-peptide antibodies. The fatty acid-derivatized amino acids are added to the C-terminal region of the peptides, in order that the resulting peptides form micelles in aqueous media. The linear, hydrophobic fatty acid chains form the micelle nucleus, while the more hydrophilic N-terminal portions of the ligand peptides are presented to antibody on the micelle periphery.

One or more amino acids can be used as spacers to separate the hydrophilic residues from the derivatized residues. Preferably, one to six neutral amino acids, selected from the group consisting of Gly, Pro, or Ser, are employed for this purpose. The amino acids to be derivatized to fatty acids are preferably selected from the group consisting of lysine and ornithine, and can be from 1 to 3 in number. Palmitic, oleic, and stearic acids are useful fatty acids; palmitic acid is preferred. The peptide antigen can be synthesized by any suitable method, for example, the Merrifield solid phase method widely employed in connection with automated peptide synthesizers. A suitable method is detailed in copending U.S. patent application Ser. No. 573,825, the disclosure of which is hereby incorporated by reference.

Alternatively, the identification peptide can be conjugated to a carrier polypeptide or protein to provide a flag immunogen. Suitable carrier proteins include globulin fractions, the serum albumins of various species, hemocyanin, ovalbumin, lactalbumin, thyroglobulin, fibrinogen, or synthetic polypeptides, for example poly(L-lysine). The number of haptens bound to the carrier protein can vary from 2 to 50, depending upon the conditions of conjugation. Preferably, a given carrier has, on average, at least five peptide haptens covalently attached. Generally, higher antibody titers are obtained using conjugates having higher epitope densities. Suitable methods for hapten-carrier conjugation are disclosed by Bauminger at al., *Methods in Enzymology* 70:151 (1980); Reichlin, *Methods in Enzymology* 70:159 (1980); Kitagawa et al., *J. Biochem.* 94:1165 (1983); and various references reviewed by Lerner, *Nature* 299:592 (1982).

Preparation of Monoclonal Antibodies

The derivatized or conjugated peptide immunogen is employed to generate monoclonal antibodies against the peptide hapten using conventional techniques, for example, those disclosed in U.S. Pat. No. 4,411,993. In this method, the immunogen is emulsified in complete Freund's adjuvant and injected in amounts ranging from 10–100 $\mu$g subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with the immunogen in the presence and absence of calcium or other divalent metal cations. Generally, metal cation concentrations in the range 0.1–10 mM are suitable. Methods for ELISA are disclosed by Engvall et al., *Immunochemistry* 8:871 (1971) and in U. S. patent application Ser. No. 573,825, previously referenced. Positive clones are then injected into the peritoneal cavities of pristane-primed syngeneic Balb/c mice to produce ascites containing high concentrations (>1 mg/ml) of anti-peptide monoclonal antibody. The resulting monoclonal antibody can be purified by ammonium sulfate precipitation followed by gel exclusion chhromatography, and/or affinity chromatography based on binding of antibody to Protein A of *Staphylococcus aureus*, or binding to immobilized identification peptide.

The following examples illustrate particular aspects of the present invention:

Example 1: Preparation of 4E11 Antibody Affinity Media

A murine hybridoma clone, designated 4E11, was isolated by screening for monoclonal antibody capable of specifically binding the DYKDDDDK flag fused to the N-terminus of human interleukin-2 (IL-2). Antibody-containing ascites produced by injection of the 4E11 hybridoma into syngeneic mice were purified and concentrated by standard methods including ammonium sulfate precipitation, affinity chromatography, and ultrafiltration. 10 ml of a purified, concentrated protein solution containing about 2.6 mg/ml 4E11 monoclonal antibody were dialyzed against 4 liters 0.1M HEPES buffer, pH 7.5, at 4° C. After about 48 hr and three changes of dialysis buffer, the contents of the dialysis tubing (about 7.5 ml) were transferred to a 50 ml polypropylene tube and held at 4° C. Affi-gel-10 ($\omega$-aminohexyl agarose; Biorad, Richmond, Calif., U.S.A.) was transferred to a sintered glass funnel and washed extensively with isopropanol followed by deionized water. Approximately 10 ml of the washed gel were added to the tube containing the antibody solution and reacted overnight on a rotator at 4° C., in accordance with the manufacturer's instructions. The following day, unreacted sites on the affinity media were blocked by adding 100 $\mu$l of 1M glycine ethyl ester, pH 8, to the media, and gently agitating for 1.5H at 4° C.

The resulting antibody-coupled gel, containing approximately 1.5 mg antibody/ml of gel, was washed with phosphate-buffered saline (PBS; 0.9M NaCl, 0.1M KHPO$_4$, pH 7.0) followed by PBS/0.02% sodium azide, and then stored at 4° C.

Example 2: Purification of Flag-BPA Fusion Protein

A yeast expression plasmid, pBC65, was constructed, comprising DNA sequences from pBR322 for selection and replication in E. coli (Ap$^r$ gene and origin of replication) and yeast DNA sequences including the TRP1 gene as a selectable marker and the yeast 2$\mu$ origin of replication. pBC65 also includes a glucose-repressible alcohol dehydrogenase 2 (ADH2) promoter, and an $\alpha$-factor leader sequence enabling secretion of heterologous proteins from a yeast host. Fused in-frame to the $\alpha$-factor leader was an inserted DNA sequence encoding a flag fusion protein comprising the DYKDDDDK sequence linked to a cDNA encoding putative human BPA (burst-promoting factor) protein. *S. cerevisiae* strains 79 and XV2181 (Trp$^-$) were transformed with pBC65 by the method of Hinnen et al., *Proc. Natl. Acad. Sci. U.S.A.* 75:1929 (1978), selecting for Trp$^+$ transformants. Transformants of each yeast strain were cloned and grown for expression in a rich medium consisting of 1% yeast extract, 2% peptone, and 1% glucose supplemented with 80 $\mu$g/ml adenine and 80 $\mu$g/ml uracil. Derepression of the ADH2 promoter and expression of the fusion protein was induced upon exhaustion of medium glucose. Crude yeast-conditioned supernatant was collected from the fermentation mixtures by filtration and held at 4° until needed.

5 ml of the 4E11 antibody-coupled affinity gel slurry prepared as described in Example 1, above, were added to a polypropylene column to provide a bed volume of about 1.5 ml. The column was then flushed with 15 ml PBS, followed by 15 ml 0.1M glycine-HC1, pH 3.0, and finally 25 ml PBS.

70 ml of the 79:pBC65 yeast-conditioned supernatant were treated by adding 7 ml 10×PBS, raising the pH of the extract to 7.12. The resulting buffered yeast supernatant was applied to the 4E11 immunoaffinity column in two 10 ml aliquots. Following sample application, the column was washed with 9 ml PBS, and stored at 4° C. overnight. The column was eluted with five 1 ml additions of 0.1M glycine-HC1, while collecting 1 ml fractions. After elution, the column was extensively washed with PBS and stored at 4° C. in PBS/0.02% sodium azide.

Samples of the wash and elution fractions were analyzed by SDS-PAGE in conjunction with Western immunoblots using silver staining of gels and 4E11 antibody. The Western transfer indicated the presence of 4E11-reactive material having an apparent molecular weight of about 28,000 daltons in the wash fractions, indicating lack of binding.

The 4E11 immunoaffinity column was then prepared for a second trial in which the wash buffers used in connection with one of the yeast supernatants was supplemented to contain 0.5 mM MgCl$_2$ and 1.0 mM CaCl$_2$. In this second experiment, two 10 ml aliquots of the 79:pBC65 yeast supernatant (pH 7.04) were applied to the column. The column was washed with PBS containing 0.5 mM MgCl$_2$/1.0 mM CaCl$_2$. The column was eluted with 0.1M glycine-HC1 as before. SDS-PAGE/Western analysis of the collected fractions indicated that the 4E11-reactive material was bound until elution with glycine-HC1. The majority of the yeast proteins were removed from the column in the wash fractions.

Example 3: Purification of Flag-GM-CSF Fusion Protein

A yeast expression vector, comprising DNA coding for the DYKDDDDK sequence fused to DNA encoding mature human granulocyte-macrophage colony stimulating factor (GM-CSF), was constructed as follows.

A 417 base pair AhaII-NcoI fragment containing the majority of the coding region and part of the 3' flanking region of the wild-type human GM-CSF gene was excised from plasmid pY$\alpha$fHuGM to provide a fragment lacking the sequence corresponding to the N-terminal 24 amino acids of the mature protein. This portion of the gene was reconstituted using an oligonucleotide which provides a revised 5' nucleotide sequence encoding an amino acid sequence coincident with the first 22 amino acids of the mature protein, but containing a 5' KpnI terminal restriction site, a BglII site at amino acid codon 4, a second NcoI site at amino acid codon 12, HpaI and HindIII sites at condons 16 and 21, respectively, and a codon substitution to provide a leucine residue at position 23. The sequence of the linker appears below:

```
                        Ala Pro Ala Arg Ser Pro
5' -CT TTG GAT AAA AGA GCT CCA GCT AGA TCT CCA
3'-CAT GGA AAC CTA TTT TCT CGA GGT CGA TCT AGA GGT
   KpnI                                 BglII

Ser Pro Ser Thr Glu Pro Trp Glu His Val Asn Ala Ile
TCT CCA TCT ACT CAA CCA TGG GAA CAC GTT AAC GCT ATT
AGA GGT AGA TGA GTT GGT ACC CTT GTG CAA TTG CGA TAA
                      NcoI          HpaI

Glu Glu Ala Leu
CAA GAA GCT TTG-3'
GTT CTT CGA AAC GC-5'
    HindIII   AhaII—>
```

The resulting construct was cloned into KpnI and NcoI-cut plasmid pBC11 (a pBR322 derivative) to generate plasmid pBC25. This plasmid is a *S. cerevisiae* expression vector substantially similar to pYαfHuGM, except for substitution of the glucose-repressible alcohol dehydrogenase 2 (ADH2) promoter for the α-factor promoter of pYαfHuGM. pBC25 was then cut with KpnI and BglII and ligated to the following oligonucleotide, which provides a DNA sequence encoding a a 3' fragment of the yeast α-factor leader sequence, fused in-frame to an *S. cerevisiae* KEX2 protease recognition site, the flag identification peptide, and the first 3-5 amino acids of mature human GM-CSF:

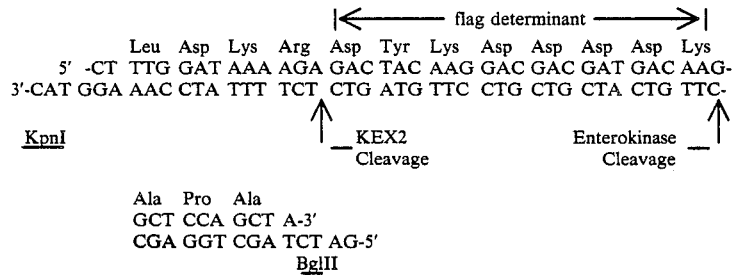

Using this vector, a fusion protein comprising the flag determinant linked to the N-terminal alanine of mature human GM-CSF is expressed and secreted by a yeast host. The α-factor secretory mechanism cleaves the translated polypeptide following the Lys-Arg KEX2 recognition site. This vector was used to transform yeast strain XV2181 by standard methods, selecting for Trp+ transformants in a selective medium consisting of 0.67% yeast nitrogen base, 0.5% casamino acids, 2% glucose, 10 μg/ml adenine and 20 μg/ml uracil.

Transformed yeast were grown in rich medium (1% yeast extract, 2% peptone, and 1% glucose supplemented with 80 μg/ml adenine and 80 μg/ml uracil) at 30° C. After removing yeast by centrifugation, the resulting conditioned medium was prepared for assay by filtering through a 0.45 μ cellulose acetate filter.

5 ml of the 4E11 antibody immunoaffinity gel slurry, prepared as described in Example 1, above, were transferred to a polypropylene column, providing a bed volume of about 1.5 ml. The column was flushed with 15 ml PBS, followed by 15 ml 0.1M glycine-HCl, pH 3, and then an additional 30 ml PBS.

11 ml of 10×PBS were added to 100 ml of yeast extract, raising the pH to about 6.9. 30 ml of the resulting diluted yeast extract were applied to the immunoaffinity column, which was then washed with five 1 ml aliquots of PBS/1 mM CaCl$_2$, with 5 minute intervals between aliquots. Fractions were collected from each application. The column was then eluted with 1.5 ml PBS, followed by four additional aliquots, each 1 ml, of PBS added hourly. 1.5 ml of PBS containing 10 mM EDTA was then added, followed by four additional 1 ml aliquots of PBS/10 mM EDTA at hourly intervals.

Finally, 4 ml glycine-HCl, pH 3, were added and collected as one fraction, which was neutralized by addition of 50 μl 1M Tris-HCl, pH 7.0. All fractions were then analyzed by SDS-PAGE followed by silver staining. The results indicated that the majority of the proteins and other contaminants present in the yeast supernatant eluted from the column in the initial wash employing PBS/1.0 mM CaCl$_2$, while the flag-GM-CSF fusion protein remained bound. The fusion protein eluted in a relatively sharp peak in the initial wash with PBS lacking Ca$^{++}$ ion. A small amount of additional material of the proper molecular weight was observed to elute from the column when the PBS/EDTA solution was applied.

The foregoing experiment was repeated substantially as described above, except that the fusion protein was eluted from the column by application of a PBS/10 mM EDTA solution following washing with PBS/1 mM CaCl$_2$. In this experiment, all detectable 4E11-reactive material eluted from the column in a sharp peak upon application of the PBS/EDTA eluant, free of other protein contaminants.

What is claimed is:

1. A process for purifying a recombinant fusion protein having a terminal peptide identification sequence comprising selected multiple anionic amino acid residues, comprising forming a complex of the protein with a divalent cation dependent monoclonal antibody specific for the sequence in the presence of a divalent cation concentration sufficient to enable formation of said complex, isolating the complex, dissociating antibody and protein by selectively depleting the concentration of divalent cations in contact with the complex and separating said protein from said antibody.

2. A process according to claim 1, wherein the identification peptide comprises from 3 to 6 aspartic acid or glutamic acid residues.

3. A process according to claim 2, wherein the divalent cation is selected from the group consisting of $Ca^{++}$, $Mg^{++}$, $Mn^{++}$, $Cu^{++}$, $Ni^{++}$, $Zn^{++}$, $Cd^{++}$, $Ba^{++}$ and $Sr^{++}$.

4. A process according to claim 3, wherein antibody and protein are dissociated by depleting cations with a chelating agent.

5. A process according to claim 4, wherein the chelating agent is EDTA or EGTA.

6. A process according to claim 5, wherein the chelating agent is EDTA.

7. A process according to claim 6, wherein the divalent cation is $Ca^{++}$.

8. A process according to claim 7, wherein the identification sequence is N-terminal DYKDDDDK.

9. A process according to claim 8, wherein the monoclonal antibody is that secreted by the murine hybridoma 4E11 (ATCC HB 9259).

10. A process for producing a fusion protein comprising a polypeptide encoded by a structural gene inserted in a prokaryotic or eukaryotic expression vector, comprising inserting adjacent to the structural gene a DNA sequence encoding a terminal identification peptide comprising selected multiple anionic amino acid residues; expressing the structural gene as a fusion protein comprising the identification peptide covalently linked to the polypeptide; separating the fusion protein from contaminants by forming a complex of the protein with a divalent cation-dependent monoclonal antibody specific for the identification peptide wherein said monoclonal antibody is capable of binding said peptide only in the presence of divalent cations and separating said protein from said antibody.

11. A process according to claim 10, wherein the identification peptide comprises from 3 to 6 aspartic acid or glutamic acid residues.

12. A process according to claim 11, wherein antibody and protein are dissociated by depleting cations with a chelating agent.

13. A process according to claim 12, wherein the chelating agent is EDTA.

14. A process according to claim 13, wherein the divalent cation is $Ca^{++}$.

15. A process according to claim 14, wherein the identification sequence is N-terminal DYKDDDDK.

16. A process according to claim 15, wherein the monoclonal antibody is that secreted by the murine hybridoma 4E11 (ATCC HB 9259).

* * * * *